(12) United States Patent
Hahn et al.

(10) Patent No.: US 12,396,951 B2
(45) Date of Patent: Aug. 26, 2025

(54) PREVENTION OF LOCAL TUMOR RECURRENCE FOLLOWING SURGERY USING SUSTAINEDAND/OR DELAYED RELEASE OF MEDICAMENTS CONTAINED IN MICRO-PARTICLES

(71) Applicant: UPEXMED CO. LTD., Anyang-si (KR)

(72) Inventors: Soon Kap Hahn, Irvine, CA (US); Gantumur Battogtokh, Incheon (KR); Oyuntuya Gotov, Incheon (KR); Gil Man Kim, Anyang (KR); Min Hyo Seo, Daejeon (KR)

(*) Notice: Subject to any disclaimer, the term of this patent is extended or adjusted under 35 U.S.C. 154(b) by 796 days.

(21) Appl. No.: 17/447,840

(22) Filed: Sep. 16, 2021

(65) Prior Publication Data

US 2022/0000782 A1    Jan. 6, 2022

Related U.S. Application Data

(63) Continuation-in-part of application No. 15/854,225, filed on Dec. 26, 2017, now abandoned.

(60) Provisional application No. 62/439,429, filed on Dec. 27, 2016.

(51) Int. Cl.
| | | |
|---|---|---|
| A61K 9/16 | (2006.01) | |
| A61K 9/50 | (2006.01) | |
| A61K 31/337 | (2006.01) | |
| A61K 31/436 | (2006.01) | |
| A61P 35/00 | (2006.01) | |

(52) U.S. Cl.
CPC .......... *A61K 9/1647* (2013.01); *A61K 9/1694* (2013.01); *A61K 31/337* (2013.01); *A61K 31/436* (2013.01); *A61P 35/00* (2018.01)

(58) Field of Classification Search
CPC .. A61K 2300/00; A61K 31/18; A61K 31/337; A61K 9/5031; A61K 9/5078; A61K 9/5084
See application file for complete search history.

(56) References Cited

U.S. PATENT DOCUMENTS

| | | | |
|---|---|---|---|
| 6,232,341 | B1 | 5/2001 | Chen et al. |
| 6,447,796 | B1* | 9/2002 | Vook .................... A61K 9/5026 424/468 |
| 7,671,095 | B2 | 3/2010 | Colson et al. |
| 8,334,324 | B2 | 12/2012 | Colson et al. |
| 8,338,492 | B2 | 12/2012 | Colson et al. |
| 8,795,707 | B2 | 8/2014 | Wolinsky et al. |
| 2010/0173005 | A1 | 7/2010 | Prestrelski |
| 2011/0223255 | A1 | 9/2011 | Thiesen |
| 2012/0121510 | A1 | 5/2012 | Brem et al. |
| 2013/0195954 | A1 | 8/2013 | Colson et al. |
| 2014/0086995 | A1 | 3/2014 | Ratner |
| 2014/0271489 | A1 | 9/2014 | Grinstaff et al. |
| 2017/0128424 | A1 | 5/2017 | Rothstein |
| 2018/0140662 | A1* | 5/2018 | Petersen .................. A61K 9/50 |
| 2019/0350867 | A1* | 11/2019 | Hahn .................... A61K 31/337 |

OTHER PUBLICATIONS

Hozumi et al.; Annals of Oncology 22: 1777-1782; published online Feb. 1, 2011.*
Quingxing Xu, Shi En Chin, Chi-Hwa Wang, Daniel W. Pack, Mechanism of Drug Release From Double-Walled PDLLA (PLGA) Microspheres, Biomaterials, May 2013, 3902-3911, vol. 34, Issue 15, Elsevier Ltd., Amsterdam.
Early Breast Cancer Trialists' Collaborative Group (EBCTCG), Effects of radiotherapy after breast-conserving surgery on 10-year recurrence and 15-year breast cancer death: meta-analysis of individual patient data for 10 801 women in 17 randomised trials, The Lancet, Nov. 2011, 1707-1716, vol. 378, issue 9804, Elsevier Ltd., Amsterdam.
Alex Sparreboom, Judith Van Asperen, Ulrich Mayer, Alfred H. Schinkel, Johan W. Smit, Dirk K. F. Meijer, Piet Borst, Willem J. Nooijen, Jos H. Beijnen, and Olaf Van Tellingen, Limited oral bioavailability and active epithelial excretion of paclitaxel (Taxol) caused by P-glycoprotein in the intestine, Mar. 4, 1997, 78-86, vol. 94, Issue 5, Proceedings of the National Academy of Sciences of the United States of America, USA.
Rong Liu MD, PHD, Jesse B. Wolinsky PHD, Joseph Walpole BS, Emily Southard MS, Lucian R. Chirieac MD, Mark W. Grinstaff PHD, Yolonda L. Colson MD, PHD, Prevention of Local Tumor Recurrence Following Surgery Using Low-Dose Chemotherapeutic Polymer Films, Annals of Surgical Oncology, 2010 1203-1213, vol. 17, Springer Nature, Switzerland.
Yasuhiro Ogura MD, Kazuhiro Mizumoto MD, PHD, Masao Tanaka MD, PHD, Kenoki Ohuchida MD, PHD, Mitsuhiko Murakami MD, PHD, Daisuke Yamada MD, Nami Ishikawa MD, Eishi Nagai MD,PHD, Strategy for prevention of local recurrence of pancreatic cancer after pancreatectomy: antitumor effect of gemcitabine mixed with fibrin glue in an orthotopic nude mouse model, Surgery, 66-71, Jul. 2006, vol. 140, Issue 1, Elsevier, Amsterdam.
Aebi S, Gelber S, Lang I, Anderson SJ, Robidoux A, Martin M, Nortier JWR, Mamounas EP, Geyer Jr. CE, Maibach R, Gelber RD, Wolmark N, Wapnir IL; International Breast Cancer Study Group, Bern, Switzerland; National Surgical Adjuvant Breast and Bowel Project, Pittsburgh, PA; Breast International Group, Brussels, Belgium, Chemotherapy prolongs survival for isolated local or regional recurrence of breast cancer: The CALOR trial (Chemotherapy, as Adjuvant for Locally Recurrent breast cancer; IBC 27-02, NSABP B-37, BIG 1-02); pp. 5-6; published Dec. 4, 2012.

(Continued)

*Primary Examiner* — Jeffrey T. Palenik
(74) *Attorney, Agent, or Firm* — CIONCA IP Law P.C.

(57) ABSTRACT

Provided herein are methods and compositions for treatment of a patient having a wound resulting from surgical resection of a tumor mass. In some embodiments, the methods provided herein include administering to the entirety of the wound area a composition before the wound area is closed, the composition having a first plurality of micro-particles comprising PLGA and one or more cancer treatment drugs, and a second plurality of micro-particles comprising PLGA and one or more wound healing drugs; wherein the wound healing drugs are released for a first period of time and the cancer treatment drugs are released for a second period of time without an initial burst release.

6 Claims, 8 Drawing Sheets

(56) References Cited

OTHER PUBLICATIONS

Hiroyuki Takabe, Moriyuki Ohkuma, Yasunori Iwao, Shuji Noguchi, Shigeru Itai, One-Step Preparation of Poly-Lactic-Co-Glycolic-Acid Microparticles to Prevent the Initial Burst Release of Encapsulated Water-Soluble Proteins, Pharmacology and Pharmacy, 2013, 578-583, Scientific Research.

Nugraha et al: "Release Retardation of Model Protein on Polyelectrolyte-Coated PLGA Nano- and Microparticles" PLOS One; vol. 9, Issue 3, Mar. 2014.

* cited by examiner

PREVENTION OF LOCAL TUMOR RECURRENCE FOLLOWING SURGERY USING SUSTAINEDAND/OR DELAYED RELEASE OF MEDICAMENTS CONTAINED IN MICRO-PARTICLES

CROSS-REFERENCE TO RELATED APPLICATIONS

This application claims the benefit and is a continuation-in-part of U.S. Non-Provisional application Ser. No. 15/854,225, filed Dec. 26, 2017, which claims the benefit of U.S. Provisional Application No. 62/439,429, filed Dec. 27, 2016, which are hereby incorporated by reference, to the extent that they are not conflicting with the present application.

BACKGROUND OF INVENTION

1. Field of the Invention

The present invention comprises a treatment process for use following cancer surgery. More specifically, the present invention comprises a local chemotherapy treatment process for use after surgery to prevent local cancer recurrence using a sustained, controlled chemotherapeutic or biologic therapy drug delivery system.

2. Description of the Related Art

There are four major types of cancer treatment: 1) surgery 2) chemotherapy 3) radiation 4) biologic therapy. If the tumor appears to be confined to one area (localized and not metastatic), surgery may be used to remove it along with any nearby tissue that might contain cancerous cells. It is often difficult to pre-determine how large the surgical resection will be. The surgeon generally makes that determination when (s)he sees the extent of the cancer during the operational procedure. Surgery is most successful when the cancer has not metastasized (spread to other organs). Surgery offers the greatest chance of cure or long-term remission for many types of cancer. However, even after surgery, cancer may recur after several years. This cancer recurrence may be due to some residual cancer cells which were not removed during the surgery. To kill these residual cancer cells, post-surgical treatments such as radiation therapy and/or systemic chemotherapy are performed. Darby et al. reported that post-surgical radiation therapy reduced the risk of recurrence during the 10 years after breast cancer surgery from 35% to 19.3% and reduced the risk of death from breast cancer from 25.2% to 21.4% over the first 15 years (Lancet, 1707-1716 (2011)). Currently many oncologists in the U.S. use the radiation therapy after lumpectomy (breast-conserving surgery) as standard procedure. However, it is expensive ($6,000-12,000) and cumbersome (4-5 weeks treatment). In addition, there are side effects, including skin burns and fatigue. Aebi et al. reported that systemic chemotherapy after surgery led to higher rates of disease-free and overall survival for women with isolated or regional recurrence of breast cancer (2012 CTRC-AACR San Antonio Breast Cancer Symposium). However, systemic chemotherapy is expensive and not successful in all treated patients. Studies in mice show that nearly 50% of systemically administered paclitaxel is excreted in the first day and less than 0.5% of the total dose remains locally available to treat cancer within the lung (Sparreboom et al. Anticancer Drugs, 78-86 (1996)). To reach effective levels locally by systemic delivery, high doses are necessary, which may lead to increased risk of systemic toxicity and morbidity.

Sustained and delayed release over several weeks of anticancer drug from a release form administered after surgery would enhance their efficacy in killing residual cancer cells without causing side effects or toxicity associated with the radiation therapy or systemic chemotherapy. Sustained release form of anticancer drug locally over several weeks would facilitate and ensure the killing of residual cancer cells at different cell cycle stages. One problem with immediately releasing an anticancer drug is that they are generally anti-proliferative and may inhibit wound healing following cancer surgery. The healing of wounds, including the wound caused by surgical resection, is a complex process that involves the activation and synchronization of many physiological events, including coagulation and inflammatory events, fibrous tissue accretion, deposition of collagen, epithelialization, wound contraction, tissue granulation and remodeling. Disruptions caused by the addition of an anti-proliferative drug such as an anticancer drug can lead to chronic wounds that are difficult to manage. Most sustained release drug delivery systems show initial burst release within the first 24-48 hours followed by sustained, uniform slow release of the encapsulated drug. This initial burst release of anticancer drug may impair wound healing. An ideal anticancer sustained, controlled release drug delivery system should possess the following properties:

1. Sustained and controlled release of the anticancer drug over 12 weeks
2. Reduced 24-48-hour initial burst of the anticancer drug
3. Acceleration of or not inhibiting wound healing during the first 7-10 days
4. Biodegradable, eliminating the need for surgical removal A local anticancer drug delivery system possessing the above properties was developed and described by Colson et al. (Annals of Surgical Oncology, 1203-1213 (2010); U.S. Pat. Nos. 7,671,095; 8,334,324; 8,338,492, 8,795,707, Publication: US 2013/0195954 and 2014/0271489). This system used a film or micro-particle form which consists of poly (glycerol monostearate-co-ε-caprolactone) and paclitaxel. The paclitaxel-loaded polymer film was implanted on the dorsum of mice after the removal of primary cancer. The paclitaxel-loaded film prevented local cancer recurrence in 83.3% of mice, compared with 12.5% of unloaded film. These inventions claim that their polymer film avoids the initial burst release of paclitaxel by functionalization of the hydroxyl group in glycerol with hydrophobic stearic acid. However, the polymer developed and used in their system is difficult to synthesize and thus possesses less commercial value. In addition, the polymer is a novel form. Regulatory authorities would require proof of safety before approving it for use in medical applications. Brem et al. (US 2012/0121510 A1) described two methods to achieve the above ideal properties; 1) designing and preparing particles which do not release anticancer drugs for approximately 2-3 weeks and administering them immediately after surgery or 2) not administering particles which release anticancer drug immediately until 2-3 weeks after surgery. Method 1) is difficult to achieve at a commercial manufacturing scale; the authors did not clearly describe how to attain such particles. Method 2) requires injection by a syringe which will be painful to patients. In addition, the injection may not distribute particles in the entire area where there may be residual tumor cells. Ogura et al. (Surgery, 66-71 (2006)) applied a mixture of gemcitabine (anticancer drug) and fibrin glue (biocompatible hemostat) to the tail of the pancreas of nude mice which were injected with SUIT-2 human pancreatic cells. This local drug delivery system aimed to demonstrate the inhibition of proliferation of residual pancreatic cancer cells. GLIADEL® wafer is the most well-known local anticancer drug delivery system manufactured and commercialized by MGI Pharma. The GLIADEL® wafer made of a biodegradable polyanhydride delivers an anticancer drug (carmustine), when placed close to the resection margins, for treating malignant glioblastoma patients after surgery. It improves the survival rate of treated patients modestly and the quality of life compared to systemic chemotherapy. However, this drug delivery system does not consider wound healing of the resected area. Therefore, there is still a need for a better drug delivery system to reduce the likelihood of cancer recurrence without inhibiting the wound healing.

The aspects or the problems and the associated solutions presented in this section could be or could have been pursued; they are not necessarily approaches that have been previously conceived or pursued. Therefore, unless otherwise indicated, it should not be assumed that any of the approaches presented in this section qualify as prior art merely by virtue of their presence in this section of the application.

BRIEF INVENTION SUMMARY

This Summary is provided to introduce a selection of concepts in a simplified form that are further described below in the Detailed Description.

In some embodiments, the present invention consists of two different types of micro-particles based on biodegradable polyester:
1. a first plurality of micro-particle (I) containing anticancer drug without the initial burst release; and
2. a second plurality of micro-particle (II) releasing wound healing drugs.

The first plurality of micro-particle (I) releases anticancer drug over 12 weeks without an initial burst release. The second plurality of micro-particle (II) releases wound healing drugs within 7-10 days to accelerate wound healing. In some preferred embodiments, the present invention utilizes polylactic glycolic acid copolymer (PLGA) containing an anticancer drug such as, but not limited to, paclitaxel or everolimus for the first plurality of micro-particle (I), and wound healing drugs such as, but not limited to, borneol and bismuth subgallate for the second plurality of micro-particle (II). All of the components in the preferred embodiment including PLGA, paclitaxel, everolimus, borneol and bismuth subgallate are accepted and approved by the U.S. FDA and many other regulatory authorities worldwide. The two micro-particles (I) and (II) in this present invention can be mixed before applying to the entire area from which the tumor was removed to deliver a predetermined amount of anticancer drug and wound healing drugs before the surgical wound is closed.

In an aspect, a method for treating a patient having a wound area resulting from surgical resection of a cancer mass is provided, the method comprising:
administering to the entirety of the wound area a composition before the wound area is closed, the composition comprising a first plurality of micro-particles comprising PLGA and one or more cancer treatment drugs, and a second plurality of micro-particles comprising PLGA and one or more wound healing drugs;
wherein the PLGA of the second plurality of micro-particles has a first ratio of PLA:PGA selectively adapted to release the one or more wound healing drugs for a first period of time;
wherein the PLGA of the first plurality of micro-particles has a second ratio of PLA:PGA selectively adapted to release the one or more cancer treatment drugs for a second period of time;
wherein the first period of time is shorter than the second period of time due to the first ratio of PLA:PGA being smaller than the second ratio of PLA to PGA;
wherein the first period of time partially overlaps with a beginning of the second period of time;
and wherein the first plurality of micro-particles is coated with a biodegradable polymer, such that to reduce an initial burst release of the cancer treatment drug by the first plurality of micro-particles.

In an aspect, a post-surgical treatment composition for administration to a wound resulting from surgical resection of a cancer mass is provided, comprising:
a first plurality of micro-particles comprising PLGA and one or more cancer treatment drugs; and
a second plurality of micro-particles comprising PLGA and one or more wound healing drugs;
wherein the PLGA of the second plurality of micro-particles has a first ratio of PLA:PGA selectively adapted to release the one or more wound healing drugs for a first period of time after the administration;
wherein the PLGA of the first plurality of micro-particles has a second ratio of PLA:PGA selectively adapted to release the one or more cancer treatment drugs for a second period of time after the administration;
wherein the first period of time is shorter than the second period of time due to the first ratio of PLA:PGA being smaller than the second ratio of PLA to PGA;
wherein the first period of time partially overlaps with a beginning of the second period of time;
and wherein the first plurality of micro-particles is coated with a biodegradable polymer, such that to reduce an initial burst release of the cancer treatment drug by the first plurality of micro-particles.

In an aspect, a method of making a post-surgical treatment composition is provided, the composition comprising micro-particles loaded with one or more post-surgical treatment drugs, the method comprising:
dissolving PLGA into dichloromethane (DCM) to obtain a first polymer solution;
adding a first post-surgical treatment drug to the first polymer solution;
pressing the first polymer solution through a membrane;
collecting a first aqueous phase resulting from the pressing step;
removing the DCM from the first aqueous phase;
obtaining a first plurality of pellets from the first aqueous phase; and
drying the first plurality of pellets;
wherein the first plurality of pellets provide a first plurality of micro-particles loaded with the first post-surgical treatment drug.

The above aspects or examples and advantages, as well as other aspects or examples and advantages, will become apparent from the ensuing description and accompanying drawings.

BRIEF DESCRIPTION OF THE DRAWINGS

For exemplification purposes, and not for limitation purposes, aspects, embodiments or examples of the invention are illustrated in the figures of the accompanying drawings, in which.

DETAILED DESCRIPTION

Figure 1A:
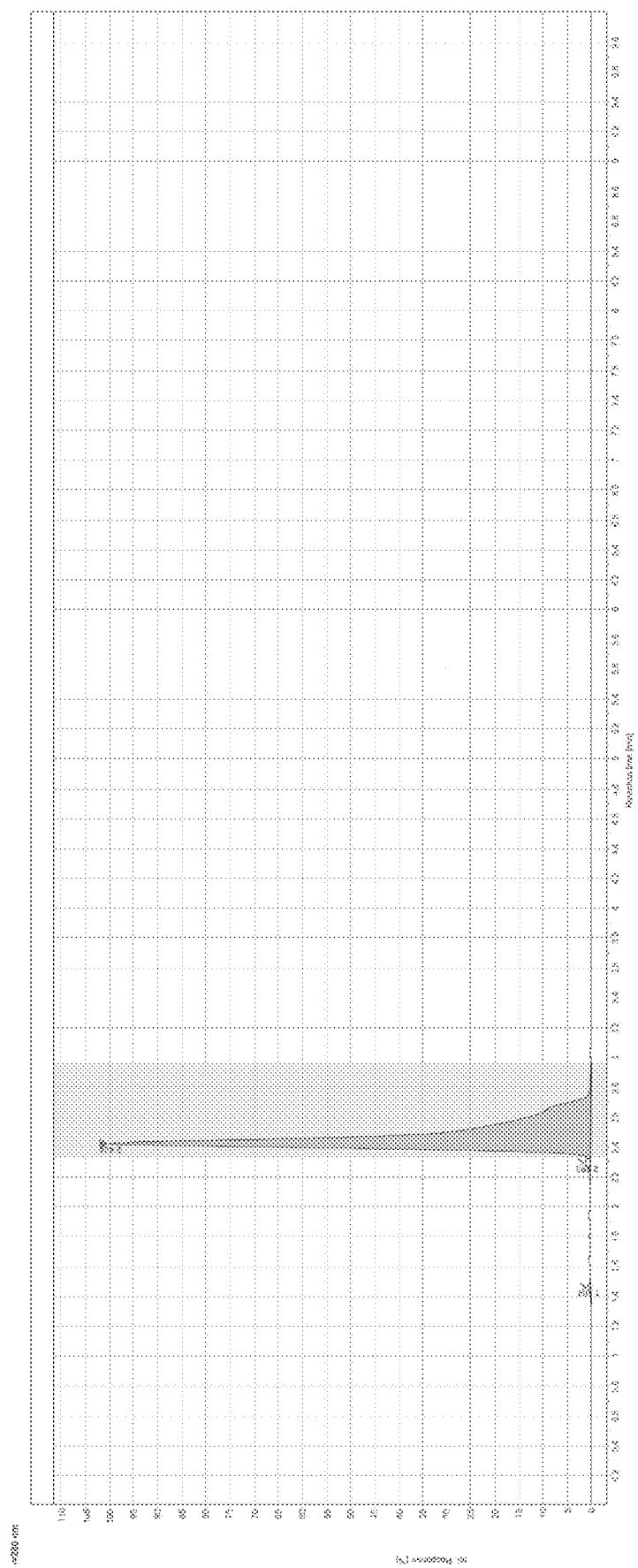
FIG. 1A depicts the HPLC analysis profile of everolimus (EVE).

What follows is a description of various aspects, embodiments and/or examples in which the invention may be practiced. Reference will be made to the attached drawings, and the information included in the drawings is part of this detailed description. The aspects, embodiments and/or examples described herein are presented for exemplification purposes, and not for limitation purposes. It should be understood that structural and/or logical modifications could be made by someone of ordinary skills in the art without departing from the scope of the invention.

It should be understood that, for clarity of the drawings and of the specification, some or all details about some structural components or steps that are known in the art are not shown or described if they are not necessary for the invention to be understood by one of ordinary skills in the art.

Provided herein are methods and compositions using micro-particles for reducing the inhibition of wound healing caused by anticancer drugs (also referred to herein as cancer treatment drugs). Also provided herein are methods and compositions wherein micro-particles loaded with cancer treatment drugs release the cancer treatment drug without an initial burst release, after micro-particles loaded with wound healing drugs have begun releasing the wound healing drugs.

Method 1 comprises use of a single type of micro-particle, which may be referred to herein as "micro-particle (I)," which releases less than 1% of an anticancer drug during the first 7 days following administration, and the remaining amount of the anticancer drug over the following 2-3 months. The anticancer drug may be any suitable anticancer drug, such as everolimus or paclitaxel. The size of each of the micro-particles may be larger than 75 μm. Micro-particle (I) may be based on a biodegradable polyester such as PLGA. These micro-particles may release a very low concentration of everolimus, paclitaxel, or other type of anticancer drug during the first 7 days post-administration. Due to the low concentration of everolimus, paclitaxel, or other anticancer drug, inhibition of wound healing may be minimal or prevented during the period of low concentration drug release. The micro-particle of Method 1 as described herein, containing an anticancer drug, may be administered locally after a tumor is removed from a patient. In addition, a breast cancer patient can take a hormone regulating drug such as exemestane or tamoxifen orally daily as a combination therapy.

Method 2 comprises use of two pluralities of different types of micro-particles, referred to herein as "micro-particle (I)" or a first plurality of micro-particles, and "micro-particle (II)" or a second plurality of micro-particles, wherein: 1) micro-particle (I) contains an anti-cancer drug without the initial burst (i.e., releasing less than 10% of anti-cancer drug within 24-48 hours); and (2) micro-particle (II) contains a wound healing drug. In some embodiments, micro-particle (I) releases an anticancer drug over 12 weeks without an initial burst release, and micro-particle (II) releases wound healing drugs within 7-10 days of administration to accelerate wound healing. In some preferred embodiments, the present invention utilizes polylactic glycolic acid copolymer (PLGA) containing an anticancer drug such as, but not limited to, paclitaxel, everolimus, or any other suitable anticancer drug, for the first plurality of micro-particle (I), and wound healing drugs such as, but not limited to, borneol, bismuth subgallate, or any other suitable wound healing drugs, for the second plurality of micro-particle (II). All of the components in the preferred embodiment including PLGA, paclitaxel, everolimus, borneol and bismuth subgallate are accepted and approved by the U.S. FDA and many other regulatory authorities worldwide. The two micro-particles (I) and (II) used for Method 2 can be mixed before application to the entire area from which a tumor was removed to deliver a predetermined amount of anticancer drug and wound healing drugs before the surgical wound is closed.

Definitions

Unless stated otherwise, technical and scientific terms used herein have the same meaning as is understood by one of ordinary skill in the art.

Micro-Particle

"Micro-particles" as used herein refers to particles having sizes between 1 μm and 500 μm and include microcapsules, microspheres and other particles. Micro-particles composed of drugs or medicaments and polymers are commonly used as a sustained, controlled release drug delivery system. Microcapsules generally have a drug core coated with a polymer film and may be spherical or non-spherical in shape. In contrast, microspheres have drugs dispersed evenly in polymer and are spherical in shape.

Polymer

Micro-particles in this invention comprise one or more biodegradable polymers and one or more anticancer drugs or wound healing drugs/medicaments. Biodegradable polymers are defined as polymers that are degradable in vivo, either enzymatically or non-enzymatically, to produce non-toxic by-products. Biodegradable polymers have become increasingly important in pharmaceutical industry especially in the field of drug delivery. Biodegradable polymers can be formulated with drugs to form a drug delivery system which can provide sustained and controlled release of drugs over days, weeks, or months. Since the drug delivery system based on biodegradable polymers degrades completely over time, it is not necessary to remove it by a surgical procedure after implanting or administration. Biodegradable polymers can be classified into natural biodegradable polymers or synthetic biodegradable polymers depending on their sources. Natural biodegradable polymers include, but are not limited to, gelatin, albumin, collagen, alginate, chitosan, derivatized cellulose, starch, hyaluronic acid and dextran. Synthetic biodegradable polymers include, but are not limited to, polyesters, polyurethanes, polyphosphazines, polyanhydrides, polycarbonates and polyesteramide. Polyesters include, but are not limited to, polylactic (PLA), polyglycolic (PGA), polycaprolactone (PCL) and their copolymers including well-known polylactic glycolic acid (PLGA). Their safety and usefulness as a drug delivery system are well-studied and accepted by regulatory authorities worldwide including the U.S. FDA. In some embodiments, the present invention uses polyesters. In a preferred embodiment, the present invention uses PLGA, a copolymer of PLA and PGA. Polyesters overall possess ideal physical and chemical properties providing ease to process, optimum drug release profile over days, weeks or months and non-toxic by-products after degradation.

Drugs or Medicaments

Anticancer drugs can be classified into chemotherapeutic drugs, targeted drugs and biological drugs. Chemotherapeutic drugs can be further classified by their mode of action:
1. alkylating;
2. antimetabolite;
3. antimicrotuble;
4. topoisomerase inhibition; and
5. cytotoxic antibiotic.

Alkylating agents include, but are not limited to, nitrogen mustards, nitrosoureas, tetrazines, aziridines, cisplatin and its derivatives, and non-classical akylating agents such as procarbazine and hexamethylmelamine. Antimetabolites include, but are not limited to, anti-folates, fluoropyrimidines, deoxynuceloside analogues and thiopurines. Antimicrotubule agents include vinca alkaloids and taxanes including paclitaxel.

Topoisomerase inhibitors include, but are not limited to, irinotecan, topotecan and other analogues. Cytotoxic antibiotics include, but not are not limited to, doxorubicin, daunorubicin, bleomycin and other analogues. Most of biological anticancer drugs try to enhance the patient's natural immune responses against cancer cells.

Chemotherapeutic drugs generally kill both cancer cells and normal healthy cells causing some serious side effects. In contrast, targeted drugs interfere with molecules (generally proteins) specific to cancer cells and eventually kill only cancer cells. The targeted drugs are more efficient and less toxic than chemotherapeutic drugs, resulting in improved overall survival rate for cancer patients. Many different targeted drugs have been approved by the FDA for use in cancer treatment. These targeted drugs include hormone therapy drugs such as tamoxifen and exemestane, signal transduction inhibitors such as everolimus (mTOR inhibitor), gene expression modulators, apoptosis inducers, angiogenesis inhibitors, immunotherapy drugs and toxin delivery molecules.

Currently, monoclonal antibodies, interleukins and interferons are types of biological anticancer drug commonly used to treat various cancers. Monoclonal antibody-based biological anticancer drugs include Herceptin®, Rituxan®, Avastin® and other agents. As a new class of anticancer drugs, monoclonal antibodies can be conjugated with chemotherapeutic drugs. Monoclonal antibodies can be designed to target cancer cells specifically. The monoclonal antibodies conjugated with chemotherapeutic drugs can take the conjugated chemotherapeutic drugs and deliver them specifically to the cancer cells but not to other cells. This limits the damage to normal cells. Examples of these types of antibodies include brentuximab vedotin (Adcetris®) and ado-trastuzumab emtansine (Kadcyla®). The current invention uses any one of the above drugs or a combination of several drugs. In a preferred embodiment, anticancer drug encapsulated in micro-particle (I) is paclitaxel or everolimus.

Wound healing drugs can be classified into small molecule drugs such as monoterpene-based or monoterpenoid-based drugs and biological drugs such as platelet-derived growth factor (PDGF) or other growth factors. The monoterpene-based or monoterpenoid-based drugs include borneol, thymol, genipin, α-terpineol and aucubin. To enhance wound healing, other synergistic component such as bismuth subgallate can be combined with the monoterpene-based drug. Sulbogin® consists of borneol and bismuth subgallate and is a wound healing product approved by the U.S. FDA in 2004 as an ointment form (U.S. Pat. No. 6,232,341). In a preferred embodiment, the present invention uses a combination of borneol and bismuth subgallate as wound healing drugs.

Excipients

Micro-particles in the present invention may also contain one or more pharmaceutically acceptable additives. The term "additive" is all components contained in micro-particles other than drugs or polymer and includes, but not limited to, buffers, preservatives and antimicrobials. It can also include hydrophilic materials such as polyethylene glycol (PEG) or polyvinylpyrrolidone (PVP) which can accelerate the biodegradation of micro-particles.

Micro-Particle Fabrication

Micro-particles in the present invention can be prepared by microencapsulation, spray drying, precipitation, hot melt microencapsulation, co-extrusion, precision particle fabrication (PPF) or other fabrication techniques. Microencapsulation techniques use single, double or multiple emulsion process in combination with solvent removal step such as evaporation, extraction or coacervation step. They are the most commonly used techniques to prepare micro-particles. The above techniques including the microencapsulation techniques can be used for water soluble drug, organic solvent soluble drug and solid powder drug. Polyesters can be processed with any one of the above techniques.

Micro-Particle (I)

Micro-particle (I) consists of polyester and anticancer drug and can be prepared with any one of the techniques described in the previous sections. Micro-particle (I) degrades slower and thus releases the contained drug longer than micro-particle (II). In a preferred embodiment, the present invention uses PLGA. Drug release rate from PLGA micro-particles can be controlled by adjusting a number of parameters such as 1) ratio between polylactic acid (PLA) and polyglycolic acid (PGA), 2) molecular weight and 3) size of micro-particle. In PLGA, polylactic acid is more hydrophobic compared to polyglycolic acid and subsequently hydrolyzes (i.e., degrades) slower. For example, PLGA 50:50 (PLA:PGA) exhibits a faster degradation than PLGA 75:25 due to preferential degradation of glycolic acid proportion if two polymers have the same molecular weights. Thus, PLGA having a smaller ratio of PLA:PGA of 50:50 generally will release contents of the micro-particles faster than PLGA having a larger ratio of 75:25.

PLGA with higher molecular weight exhibits a slower degradation rate than PLGA with lower molecular weight. Molecular weight has a direct relationship with the polymer chain size. Higher molecular weight PLGA has longer polymer chain and requires more time to degrade than lower molecular weight PLGA. In addition, an increase in molecular weight decreases drug diffusion rate and therefore drug release rate. The size of micro-particle also affects the rate of drug release. As the size of micro-particle decreases, the ratio of surface area to volume of the micro-particle increases. Thus, for a given rate of drug diffusion, the rate of drug release from the micro-particle will increase with decreasing micro-particle size. In addition, water penetration into smaller micro-particle may be quicker due to the shorter distance from the surface to the center of the micro-particle.

The delivered PLGA micro-particle (I) degrades and releases anticancer drug over 12 weeks to the cancer removal area and kills any residual cancer cells. Most chemotherapeutic drugs work by impairing mitosis (cell division). Most of cancer cells exhibit cell cycles of several days to several weeks. Therefore, effective drug delivery systems should release anticancer drugs over a long period (>4 weeks) to avoid the escape of cancer cells, which may become a source of cancer recurrence. Micro-particle (I) in the present invention can be prepared with PLGA 1) a portion of PLA equal to or greater than 50%, 2) molecular weight (Mw)>35,000 and 3) micro-particle size larger than 1 μm. Preferably the size of micro-particle (I) is larger than 50 μm. Typical composition of micro-particles (I) in this invention is 60-95% of PLGA and 5-40% of anticancer drug. In a preferred embodiment, the present invention uses paclitaxel or everolimus as anticancer drug.

Coating of Micro-Particle (I)

Micro-particle (I) in this invention can be coated with a biodegradable polymer to reduce the initial burst release of anticancer drug. The coating biodegradable polymer can be the same polymer used in micro-particle (I) or different polymer. Coating of micro-particle (I) can be done by various methods such as a coating method through the phase separation of coating polymer on the surface of PLGA micro-particles using emulsion-solvent evaporation method (H. Takabe et al. Pharmacology & Pharmacy, 578-583 (2014)) or a double-walled micro-particle fabrication method (Q. Xu et al. Biomaterials, 3902-3911 (2013)).

Micro-Particle (II)

Micro-particle (II) consists of polyester and wound healing drugs and can be prepared with any one of the techniques described in the previous sections. Micro-particle (II) degrades much faster than micro-particle (I) and releases wound healing drugs during the first 7-10 days. In a preferred embodiment, the present invention uses PLGA. Micro-particle (II) can be prepared with PLGA 1) PLA:PGA 50:50 2) molecular weight (Mw)<35,000 and 3) micro-particle size<50% of micro-particle (I) size. Preferably the size of micro-particle (II) is smaller than 50 μm. Typical composition of micro-particle (II) in this invention is 60-95% of PLGA and 5-40% of combined wound healing drugs. In some embodiments, micro-particle (II) contains borneol (monoterpene, 0.5-5%) and bismuth subgallate (1-10%) as wound healing drugs. Sulbogin® consisting of both drugs was approved by the U.S. FDA in 2004 as an ointment form for daily application and commercialized in the U.S. It is advantageous to use the drugs approved by the U.S. FDA. In a preferred embodiment, micro-particle (II) can be prepared with the same composition of borneol (0.7%) and bismuth subgallate (4.5%) used in Sulbogin®.

Micro-Particle Delivery

Coated-micro-particle (I) and micro-particle (II) are mixed at a ratio of coated-micro-particle (I) to micro-particle (II) less than 0.5 and preferably 0.25 to make sure that the release amount of wound healing drugs surpasses that of anticancer drug during the first 7-10 days. The combined micro-particles (I) and (II) should be administered uniformly to the entire cancer removal area to avoid the overdose of some area. The amount of delivered micro-particles should be determined and adjusted depending on the size of the cancer removal area.

Fabrication of Micro-Particle (I) by Microencapsulation Technique

Micro-particle (I) can be prepared by oil-in-water emulsion and solvent evaporation processes. Briefly, paclitaxel (50 mg) is dissolved in a solution of PLGA (0.5 g; 75:25; Mw=~100,000) in 5 mL of dichloromethane. The organic solution is added into 20 mL of 1% polyvinyl alcohol (PVA) aqueous solution. PVA is used to stabilize the emulsified micro-particles and prevent micro-particle fusion during the emulsion process. The resulting solution is rapidly homogenized using a homogenizer for 30 sec. The size of micro-particles can be controlled by the speed of the homogenizer. The mixture is then diluted with 0.1% PVA with a final volume of 500 mL, and stirred at 1000 rpm at room temperature and ambient pressure until the solvent evaporation is completed. The micro-particles are collected by centrifugation and washed with cold deionized water. The resulting micro-particles are then frozen using dry ice and dried in a lyophilizer.

Coating of Micro-Particle (I)

The lyophilized micro-particle (I, 1 g) as prepared above is dispersed in 150 mL of a 0.1% PVA aqueous solution, and the resulting dispersion is added to 2 mL of a PLGA coating solution consisting of 100 mg of PLGA dissolved in 2 mL of acetone. The mixture is then stirred for 3 hours at 40° C. The micro-particle (I) coated with PLGA is washed with cold deionized water and lyophilized. The lyophilized micro-particle (I) is stored at 4° C.

Fabrication of Micro-Particle (II) by Co-Extrusion Technique

PLGA (50:50; Mw=~15,000) in the form of granules is first milled at lower than 0° C. and sieved to obtain micro-particles having an average grain size of 180 μm or less. To this powder mass (10 g), is added finely pulverized borneol (70 mg; melting point=208° C.), bismuth subgallate (450 mg; melting point=223° C.) and other additives such as boric acid as a buffer and benzenesulfonamide (melting point=151° C.) as antimicrobial. The average grain size of two drugs and two additives is approximately 10 μm. The resulting mixture is homogenized in a mill at room temperature. The homogenized mixture is then extruded at 80-100° C. with a diameter of approximately 1.5 mm. The obtained rods are left to cool at room temperature, cut into small pieces and finally milled at −30° C. After sieving, micro-particle (II) with an average size of 25 μm or less but larger than 1 μm is collected. The resulting micro-particle (II) is stored at 4° C.

Final Formulation

Micro-particle (I, 0.5 g) and micro-particle (II, 2 g) are mixed thoroughly and the resulting mixture is applied to the area from which the tumor was removed.

Post-Surgical Treatment Compositions

Provided herein are post-surgical treatment compositions for administration to a wound resulting from surgical resection of a cancer mass, comprising any of the micro-particles disclosed herein. In some embodiments, the composition comprises:

a first plurality of micro-particles comprising PLGA and one or more cancer treatment drugs; and a second plurality of micro-particles comprising PLGA and one or more wound healing drugs;

wherein the PLGA of the second plurality of micro-particles has a first ratio of PLA:PGA selectively adapted to release the one or more wound healing drugs for a first period of time after the administration;

wherein the PLGA of the first plurality of micro-particles has a second ratio of PLA:PGA selectively adapted to release the one or more cancer treatment drugs for a second period of time after the administration;

wherein the first period of time is shorter than the second period of time due to the first ratio of PLA:PGA being smaller than the second ratio of PLA to PGA;

wherein the first period of time partially overlaps with a beginning of the second period of time;

and wherein the first plurality of micro-particles is coated with a biodegradable polymer, such that to reduce an initial burst release of the cancer treatment drug by the first plurality of micro-particles.

In some embodiments, the first plurality of micro-particles has an increased physical size to induce a reduced rate of release of the one or more cancer drugs during the second period of time. In some embodiments, the first plurality of micro-particles has an increased physical size to induce a reduced rate of release of the one or more cancer drugs during the second period of time. In some embodiments, the first plurality of micro-particles has a diameter size of about 75 μm or larger. In some embodiments, the PLGA of the second plurality of micro-particles has a decreased molecular weight to induce an increased rate of release of the one or more wound drugs during the first period of time. In some embodiments, the second period of time begins about 7 days after the administering step, and the first plurality of micro-particles releases about 1% or less of the one or more cancer treatment drugs before the second period of time begins. In some embodiments, the first ratio of PLA:PGA is 50:50, and the second ratio of PLA:PGA is 75:25.

Post-Surgical Treatment Composition Preparation Methods

Provided here are methods of making a post-surgical treatment composition comprising any of the micro-particles disclosed herein, loaded with one or more post-surgical treatment drugs. In some embodiments, the method comprises:

dissolving PLGA into dichloromethane (DCM) to obtain a first polymer solution;

adding a first post-surgical treatment drug to the first polymer solution;

pressing the first polymer solution through a membrane;

collecting a first aqueous phase resulting from the pressing step;

removing the DCM from the first aqueous phase;

obtaining a first plurality of pellets from the first aqueous phase; and drying the first plurality of pellets;

wherein the first plurality of pellets provide a first plurality of micro-particles loaded with the first post-surgical treatment drug.

In some embodiments, the method further comprises:

dissolving PLGA into dichloromethane (DCM) to obtain a second polymer solution;

adding a second post-surgical treatment drug to the first polymer solution;

pressing the second polymer solution through a membrane;

collecting a second aqueous phase resulting from the pressing step;

removing the DCM from the second aqueous phase;

obtaining a second plurality of pellets from the second aqueous phase; and drying the second plurality of pellets;

wherein the second plurality of pellets provide a second plurality of micro-particles loaded with the second post-surgical treatment drug.

In some embodiments, the method comprises mixing the first plurality of micro-particles and the second plurality of micro-particles. In some embodiments, the mixing step occurs immediately before administration to a patient in need thereof.

In some embodiments, the membrane comprises a pore size of about 10 to about 50 μm. In some embodiments, the pore size is about 50 μm, and the micro-particles are about 75 μm or larger in diameter. In some embodiments, the membrane has a pore size of about 50 μm, and the micro-particles are about 75 μm or larger in diameter. In some embodiments, the obtaining steps are performed by filtering using a filter paper or centrifugation.

In some embodiments, the one or more post-surgical treatment drugs are selected from: wound healing drugs, and cancer treatment drugs. In some embodiments, the micro-particles comprise a drug loading percentage of the wound healing drug or the chemotherapy drug of about 5%, about 10%, about 15%, about 20%, about 30%, about 40%, about 50%, or about 60%. In some embodiments, the one or more post-surgical treatment drugs is everolimus or paclitaxel.

Treatment of Patients after Surgical Resection

Provided herein are methods for treatment of a patient in need thereof with any of the compositions disclosed herein. In some embodiments, the patient has a wound resulting from surgical resection. In some embodiments, the methods are for treating a patient having a wound area resulting from surgical resection of a cancer mass. In some embodiments, the method comprises:

administering to the entirety of the wound area a composition before the wound area is closed, the composition comprising a first plurality of micro-particles comprising PLGA and one or more cancer treatment drugs, and a second plurality of micro-particles comprising PLGA and one or more wound healing drugs;

wherein the PLGA of the second plurality of micro-particles has a first ratio of PLA:PGA selectively adapted to release the one or more wound healing drugs for a first period of time;

wherein the PLGA of the first plurality of micro-particles has a second ratio of PLA:PGA selectively adapted to release the one or more cancer treatment drugs for a second period of time;

wherein the first period of time is shorter than the second period of time due to the first ratio of PLA:PGA being smaller than the second ratio of PLA to PGA;

wherein the first period of time partially overlaps with a beginning of the second period of time;

and wherein the first plurality of micro-particles is coated with a biodegradable polymer, such that to reduce an initial burst release of the cancer treatment drug by the first plurality of micro-particles.

In some embodiments, the first plurality of micro-particles and the second plurality of micro-particles are mixed at a ratio of less than 0.5 by weight. In some embodiments, the first plurality of micro-particles has an increased physical size to induce a reduced rate of release of the one or more cancer drugs during the second period of time. In some embodiments, the first plurality of micro-particles has a diameter size of about 75 μm or larger. In some embodiments, the PLGA of the first plurality of micro-particles has an increased molecular weight to induce a reduced rate of release of the one or more cancer drugs during the second period of time. In some embodiments, the second plurality of micro-particles has a decreased physical size to induce an increased rate of release of the one or more wound drugs during the first period of time. In some embodiments, the PLGA of the second plurality of micro-particles has a decreased molecular weight to induce an increased rate of release of the one or more wound drugs during the first period of time. In some embodiments, the second period of time begins about 7 days after the administering step, and the first plurality of micro-particles releases about 1% or less of the one or more cancer treatment drugs before the second period of time begins. In some embodiments, the first ratio of PLA:PGA is 50:50, and the second ratio of PLA:PGA is 75:25.

EXAMPLES

The following examples relate to the preparation, characterization, and analysis of micro-particles comprising wound healing and anticancer drugs for the use of treatment after resection for a tumor. Experiments were carried out to demonstrate that postsurgical local treatment with an anticancer drug may reduce the rate of cancer recurrence after tumor removal. Everolimus (EVE) and paclitaxel (PTX) were selected as model anticancer drugs. Both drugs were approved by the US FDA for treatment of various cancer types. EVE is a so-called targeted drug which specifically inhibits mechanistic target of rapamycin (mTOR) in the phosphoinositide 3-kinase (PI3K) pathway. Over-activation of mTOR is often implicated in cancer. EVE was approved by the US FDA in combination with exemestane (an aromatase inhibitor, and an estrogen modulator) for treating hormone positive and HER2 negative breast cancer patients after surgical removal of tumor tissue to reduce the rate of breast cancer recurrence. This combination drug is taken orally, but shows some serious cumulative systemic side effects.

Various combination therapies were tested in MCF-7 (breast cancer cell line) tumor bearing mice, using EVE-loaded PLGA microspheres, to demonstrate reduction in systemic side effects while lowering the rate of breast cancer recurrence. Local administration of EVE-loaded PLGA microspheres was tested with either an oral administration of exemestane, or an oral administration of tamoxifen (another estrogen modulator).

Next, local administration of PTX-loaded PLGA microspheres combined with oral administration of exemestane or tamoxifen were also tested. PTX is a so-called chemotherapy drug which kills cancer cells as well as normal cells. Since it kills the normal cells along with the cancer cells, it can result in more side effects than EVE.

Example 1: Preparation and Characterization of EVE- or PTX-Loaded PLGA Microspheres (E10PA52, E10PA53, E20PA53, E10PE77, E20PE77, P15PA53 and P15PE77)

The preparation and characterization of EVE- and PTX-loaded PLGA microspheres and the methods for the use of the microspheres in the MCF-7 tumor bearing mice model study are as follows.

PLGA microspheres were prepared with different properties, including drug release profiles. Microspheres with the nomenclature E10PA52, E10PA53, E20PA53, E10PE77, E20PE77, P15PA53 and P15PE77 were prepared. In the nomenclature, "E" refers to everolimus and "P" refers to paclitaxel; the 10 or 15 denotes that 100 mg of EVE or 150 mg of PTX were added into a solution of 1 g PLGA in 9 mL of dichloromethane (DCM); "PA" and "PE" denote acid-terminated PLGA and ester-terminated PLGA, respectively; 5 and 7 denote that the ratio of lactide:glycolide is 50:50 and 75:25, respectively; and 2 and 7 denote a molecular weight of 15,000 daltons (15 kDa) and 75,000 daltons (75 kDa), respectively.

PLGA (1 g) was dissolved in 9 mL of dichloromethane (DCM) by stirring at room temperature (RT) for 1 hour (h). To the polymer solution, EVE (100, 200, or 500 mg) or PTX (150 mg) was added and stirred for an additional 10 minutes. The solution (oil phase) was poured into the dispersion phase tank of a Shirasu Porous Glass (SPG) membrane machine (manufactured by MCTech) and pressed through a ceramic membrane having a pore size of 10, 20, 30 or 50 μm, using nitrogen gas into the continuous phase tank filled with 4% polyvinyl alcohol (PVA) solution. The process was carried out for about 2 h. The aqueous phase was collected in a glass beaker and stirred with a propeller stirrer for 4 h at RT to remove the DCM. Next, cold distilled water (DIW, 500 mL) was added to the microsphere solution and filtered by 20 μm filter paper or centrifuged at 3,000 rpm for 5 minutes after cooling down for 2-6 h at 4° C., followed by washing with cold water (1 L). The collected pellets were freeze-dried for about 24-48 h and vacuum dried for about 72-96 h at 39° C. in a vacuum oven.

Preparation of Standard Curves for Everolimus and Paclitaxel and Analysis by High Performance Liquid Chromatography (HPLC)

A stock solution of EVE (1 mg/mL) was prepared in a high performance liquid chromatograph (HPLC) mobile phase, acetonitrile (AN) and 0.1% phosphoric acid solution at a ratio of 95:5. Next, using the stock solution, a series of concentrations of EVE solution (1.25, 2.5, 6.25, 12.5, 25, 50, and 100 μg/mL) were obtained and filtered through a 0.45 μm syringe filter. Analyses of these EVE solutions were carried out by the HPLC system with a C18 column (Agilent Poroshell 120 EC-C18; 4.6×150 mm, 5 μm) connected with a UV detector to obtain standard curves. EVE was detected at the 280 nm wavelength and having a 2.42 minute retention time.

For the PTX, a stock solution with a concentration of 1 mg/mL was prepared in AN. Next, a series of concentrations of PTX were prepared from the stock solution (0.16, 0.8, 4, 20, 100 μg/mL) in a mobile phase. As a mobile phase, AN and 0.1% phosphoric acid solution at a ratio of 65:35 was used. Analyses of these PTX solutions were carried out by the HPLC system with the same C18 column described above to obtain standard curves. PTX was detected at the 227 nm wavelength and its retention time was 2.78 minutes.

Measurement of the Content of Everolimus and Paclitaxel in Microsphere

In order to determine the content of EVE and PTX in the microsphere (MS), a certain amount of EVE-PLGA MS or PTX-PLGA MS was weighed and dissolved in AN via 10 min-sonication. These solutions were diluted with mobile phase and measured by HPLC. The drug encapsulation efficiency (EE) and drug loading content (LC) were calculated by the following equations:

$$EE\ (\%) = \frac{\text{Weight of found Drug}}{\text{Weight of feed Drug}} \times 100$$

$$LC\ (\%) = \frac{\text{Weight of found Drug}}{\text{Weight of feed Drug} + \text{Feed } PLGA} \times 100$$

In Vitro Release Study of EVE-PLGA Microsphere

The in vitro release study was carried out by a sample-and-separate method. Briefly, 20 mg of microsphere sample (n=3) was taken in a 100 mL flask and dispersed in 50 mL of release medium (0.5% Tween 20 and 0.1% sodium azide in phosphate buffered saline (PBS) at pH 7.4). The flasks were placed in an orbital agitating incubator at 37° C. and shaken at 100 rpm. At certain time points (E10PA53 at 1, 3, 7, 14, 21, 28, 35, 42, 49, 56 days and E10PE77 at 1, 3, 7, 14, 21, 28, 35, 42, 49, 56, 63, 70, 77, 84, 91 days), all medium was collected and filtered on filter paper. The filtered pellet was freeze-dried for 24 h and dissolved in acetonitrile. The content of the unreleased EVE was then analyzed by HPLC as described above. Since EVE was known to be degradable in aqueous solution as a free form in a time-dependent manner, the EVE content was analyzed in the microsphere residue. It was confirmed that there was no change in the stability of EVE in the microsphere.

In Vitro Release Study of PTX-PLGA Microsphere

The in vitro release study was carried out by a sample-and-separate method. Briefly, 30 mg of microsphere sample (n=3) was taken in a 100 mL flask and dispersed in 50 mL of release medium (0.5% Tween 20 and 0.1% sodium azide in PBS at pH 7.4). The flasks were placed in an orbital agitating incubator at 37° C. and shaken at 100 rpm. At certain time points (1, 3, 7, 10, 14, 21, 28, 35, 42, 49, 56, 63, 70, 77, 84, 91 days), 40 mL medium was taken and centrifuged at 3,000 rpm for 2 min. From the supernatant, 30 mL was pipetted and replaced by same amount of fresh media. In the collected supernatant, the content of the released PTX was analyzed by HPLC.

Results

EVE-loaded PLGA polymer microspheres were prepared using an acid-terminated PLGA with a molecular weight of 15 kDa and 30 kDa and a ratio of lactide and glycolide of 50:50, and using an ester-terminated PLGA with a molecular weight of 50 kDa and 75 kDa and a ratio of lactide and glycolide of 50:50 and 75:25. Four types of membranes were used, having pore sizes of 10 μm, 20 μm, 30 μm and 50 μm, to produce different sizes of microspheres.

Various PLGA polymers were used to create microspheres with different release profiles for EVE (from 3 weeks to 3 months). In general, the ester-terminated PLGA polymers are more hydrophobic than the acid-terminated PLGA polymers and subsequently they degrade slower and release the encapsulated drug slower than the acid-terminated PLGA polymers.

The EVE- or PTX-PLGA MS were prepared via oil-in-water (O/W) emulsion and a solvent evaporation method using a Shirasu-porous-glass (SPG) membrane machine with a yield of about 67-93% (summarized in Table 1 below). The EVE-PLGA MS was prepared with a target drug loading of 10%, 20%, and 50% (E10PA52, E10PA53, E50PA53, E10PE55, E10PE77, and E20PE77) and actual loading contents for the EVE-PLGA MSs were found to be around 5-14% (Table 1).

FIG. 1A depicts the HPLC analysis profile of everolimus (EVE). The EVE content was analyzed by HPLC method as described previously, and the retention time was 2.42 minutes.

Figure 1B:
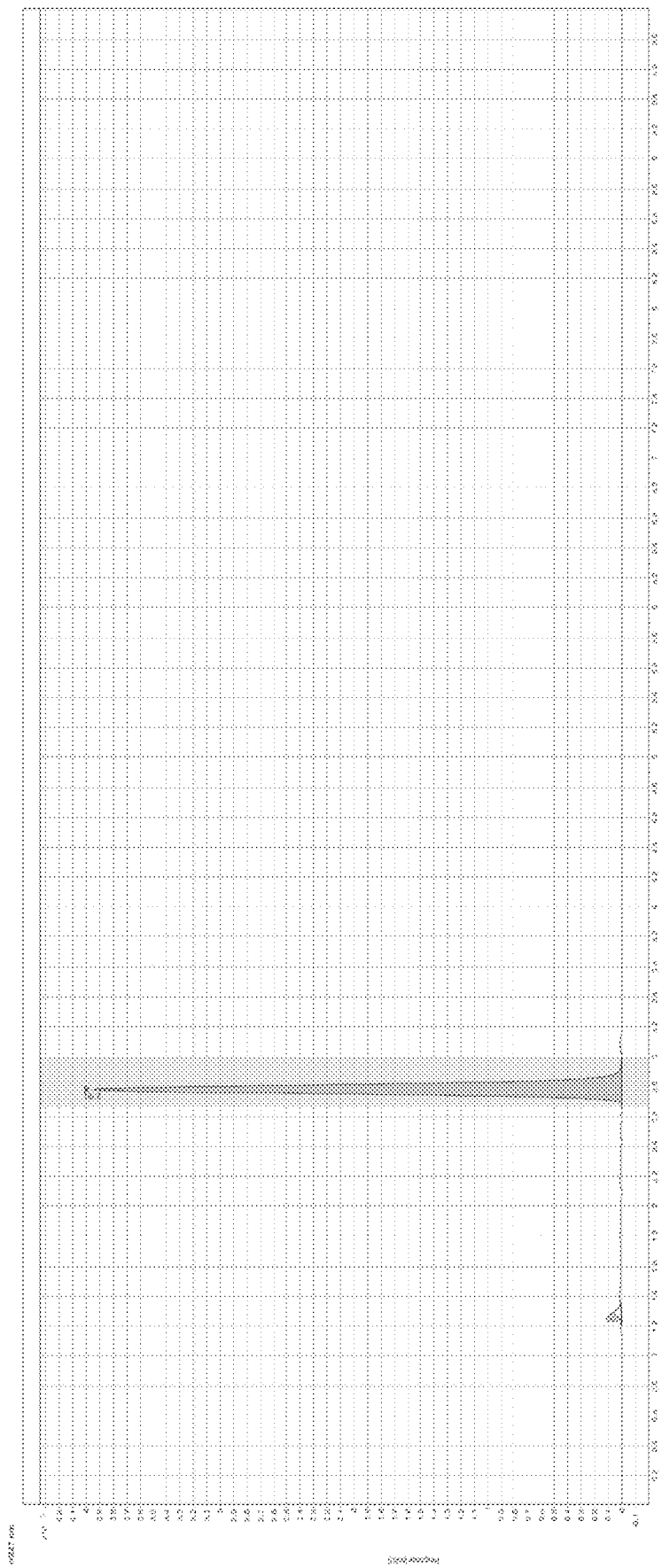
FIG. 1B depicts the HPLC analysis profile of paclitaxel (PTX).

FIG. 1B depicts the HPLC analysis profile of paclitaxel (PTX). The PTX content was analyzed by HPLC method as described previously, and the retention time was 2.78 minutes.

Figure 2B:
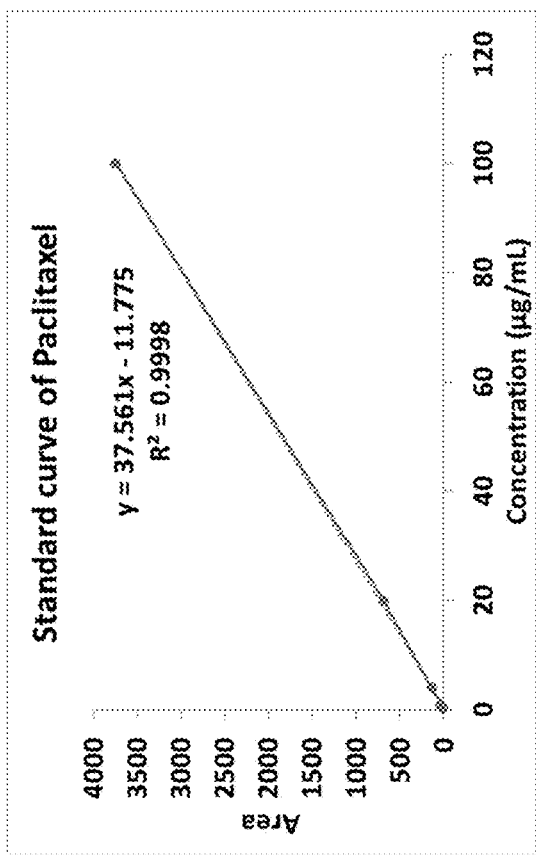
FIGS. 2A-2B depict the standard curves obtained for everolimus (EVE) and paclitaxel (PTX), respectively, of EVE- and PTX-loaded microspheres.
Figure 2A:
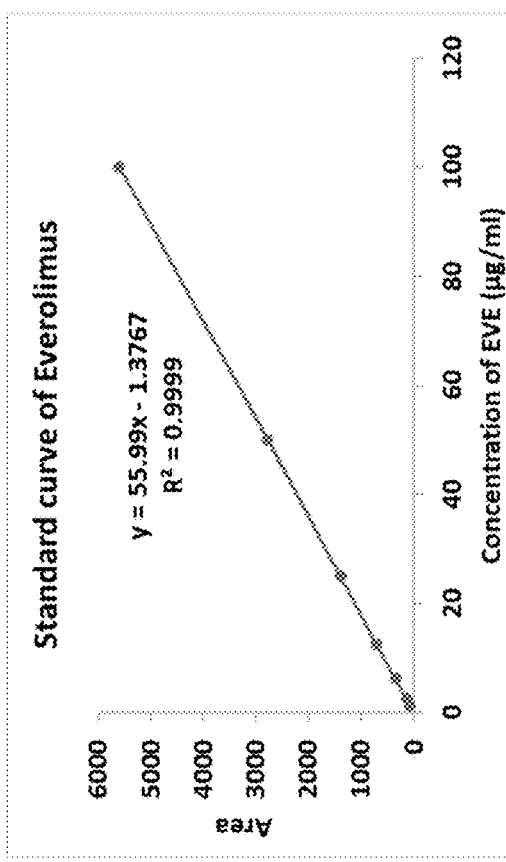

FIGS. 2A-2B depict the standard curves obtained for everolimus (EVE) and paclitaxel (PTX), respectively, of EVE- and PTX-loaded microspheres. The standard curve for EVE was prepared by HPLC at a 1.25-100 μg/mL concentration range and the correlation coefficient (R) was 0.9999. In order to completely dry the microspheres and remove the organic solvent, 48 h-lyophilization and 48 h-vacuum drying at a lower temperature than the transition temperature of the polymer were carried out.

Figure 3B:
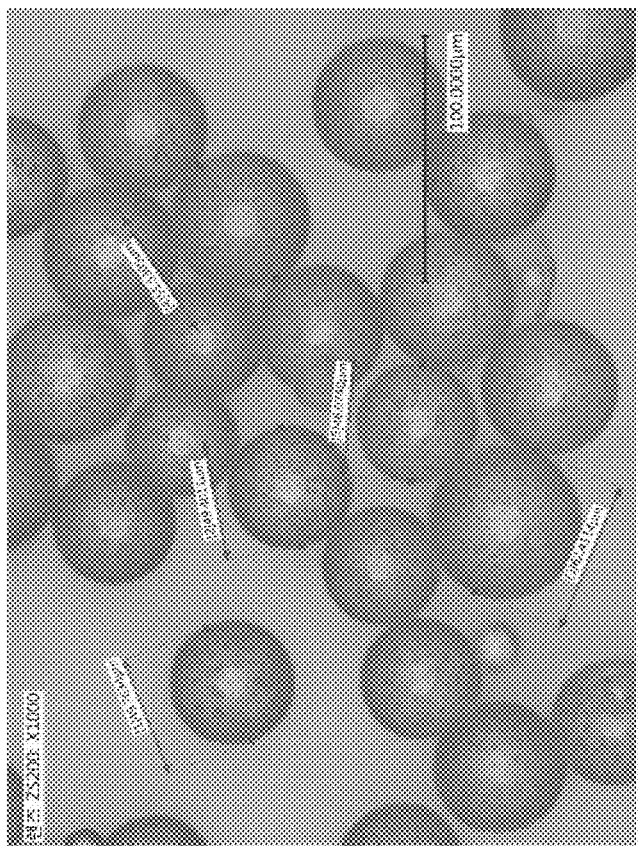
FIGS. 3A-3B depict images of EVE-PLGA microspheres (MS) prepared with different membranes, taken by optical microscope, showing the general size and morphology of the microspheres.
Figure 3A:
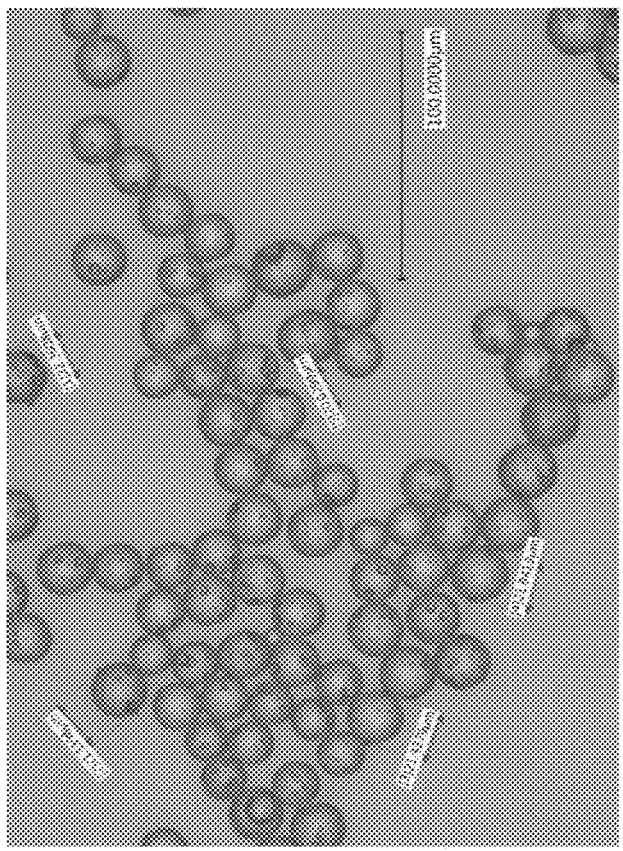

FIGS. 3A-3B depict images of EVE-PLGA microspheres (MS) prepared with different membranes, taken by optical microscope, showing the general size and morphology of the microspheres. FIG. 3A depicts the E10PA52 type MS, resulting from preparation with a 10 μm membrane, and FIG. 3B depicts micro-particles resulting from preparation with a 30 μm membrane. The microspheres prepared with membranes having 10 and 30 μm pore sizes were analyzed as having a 20-30 μm and 40-60 μm diameter size, respectively, and were observed having a spherical morphology, as depicted by the optical microscope images.

The microspheres were also prepared using a membrane with a pore size of 50 μm, which produced microspheres having a diameter size larger than 75 μm. To analyze the release behavior of EVE from the microspheres, an in vitro release study was performed by a sample-and-separate method at physiological conditions. Since everolimus is known to be less stable in aqueous solution for a longer time, the amount of EVE released from microspheres was analyzed in a reverse manner. The content of EVE was determined in the remaining microsphere after collecting whole samples at certain time points to avoid degradation-related loss of EVE in an aqueous environment.

Figure 4B:
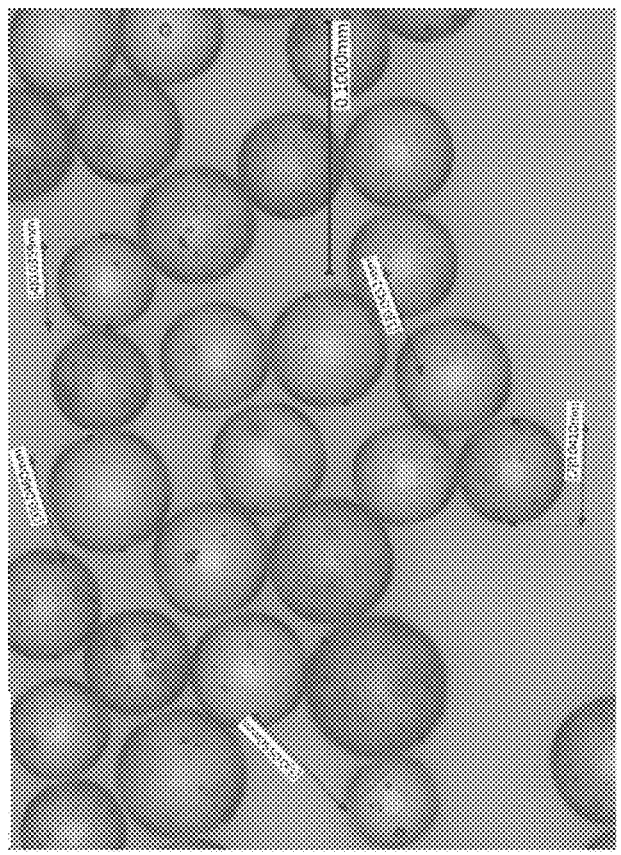
FIGS. 4A-4B depict images of PTX-PLGA MS prepared with 30 μm membranes, taken by optical microscope, showing the general size and morphology of the microspheres.
Figure 4A:
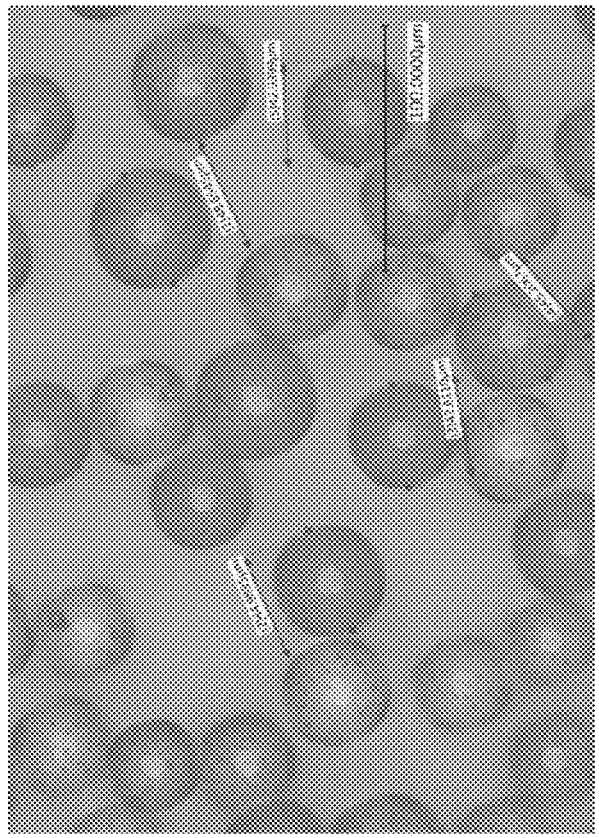

FIGS. 4A-4B depict images of PTX-PLGA MS prepared with 30 μm membranes, taken by optical microscope, showing the general size and morphology of the microspheres. FIG. 4A depicts the P15PA53 type MS, and FIG. 4B depicts the P15PE77 type MS. As with the EVE-PLGA MS, the PTX-PLGA MS were observed having a spherical morphology, as depicted by the optical microscope images.

Example 2

Figure 5:
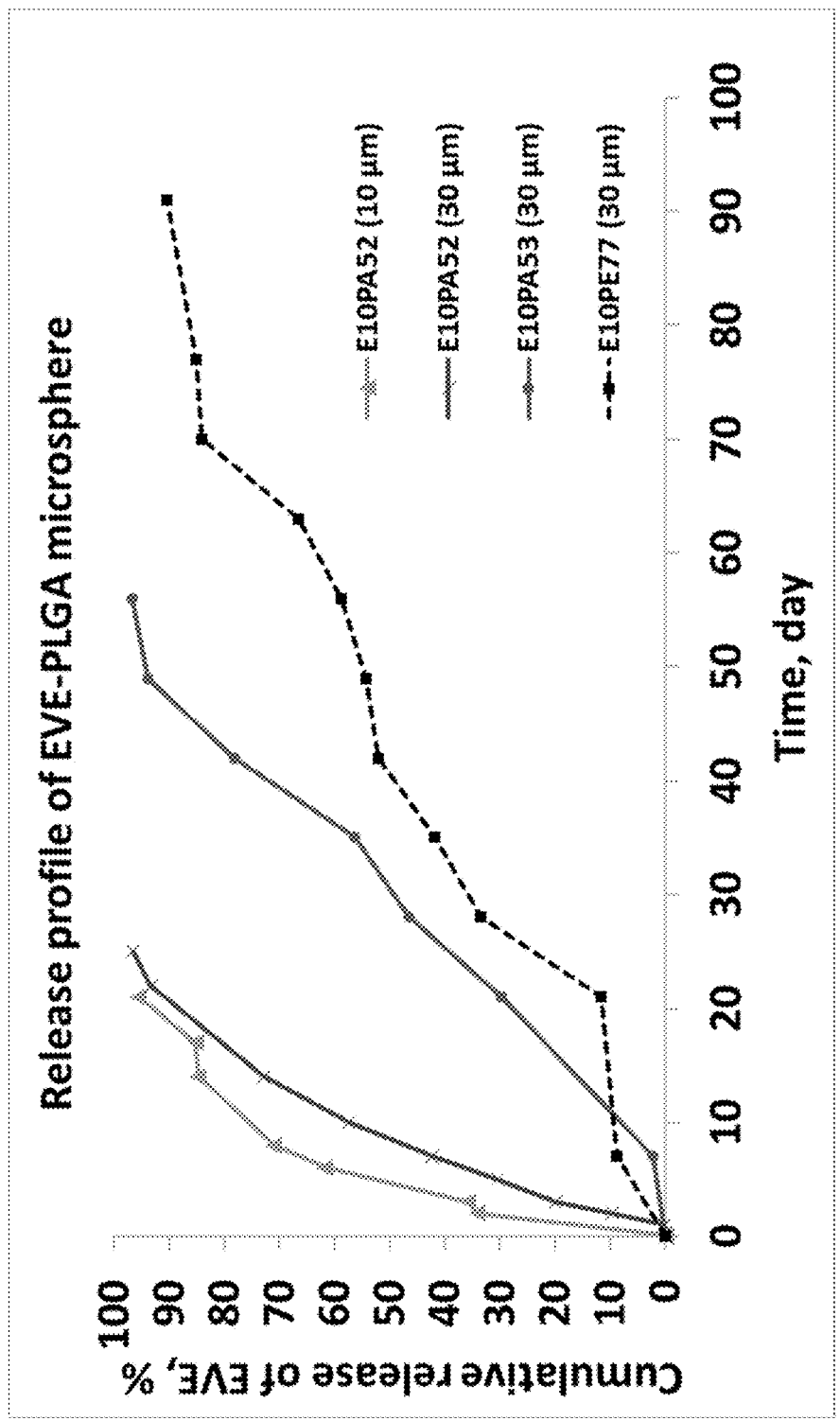
FIG. 5 is a line graph depicting the in vitro release profiles of cumulative EVE percentage from various PLGA microspheres, over a period of about 90-100 days.

FIG. 5 is a line graph depicting the in vitro release profiles of cumulative EVE percentage from various PLGA microspheres, over a period of about 90-100 days. It was found that EVE was released in 21 days from E10PA52 (prepared with 10 μm membrane; MW=15 kDa), 25 days from E10PA52 (prepared with 30 μm membrane; MW=15 kDa), 56 days from E10PA53 (prepared with 30 μm membrane; MW=30 kDa), and 98 days from E10PE77 (prepared with 30 μm membrane; ester terminated; LA:GA=75:25 and MW=75 kDA), respectively It was shown that the release rate of EVE was directly correlated to the molecular weight of the polymer and ratio of the monomer (lactide:glycolide) as well as the size of the microsphere. In this release study, it was found that increasing the size of the microspheres (larger than 75 μm in diameter) significantly reduced the release rate of anti-cancer drug encapsulated in PLGA microspheres during the first 7 days. Generally, an anti-cancer drug is an antiproliferative which may inhibit wound healing. Since wound healing at resected areas occurs during the first 7 days after surgical removal, it is generally not desirable to release a high concentration of an anti-cancer drug during this period. It was found that microspheres with a size larger than 75 μm in diameter did not release almost any anti-cancer drug encapsulated in the PLGA microspheres during the first 7 days.

Figure 6:
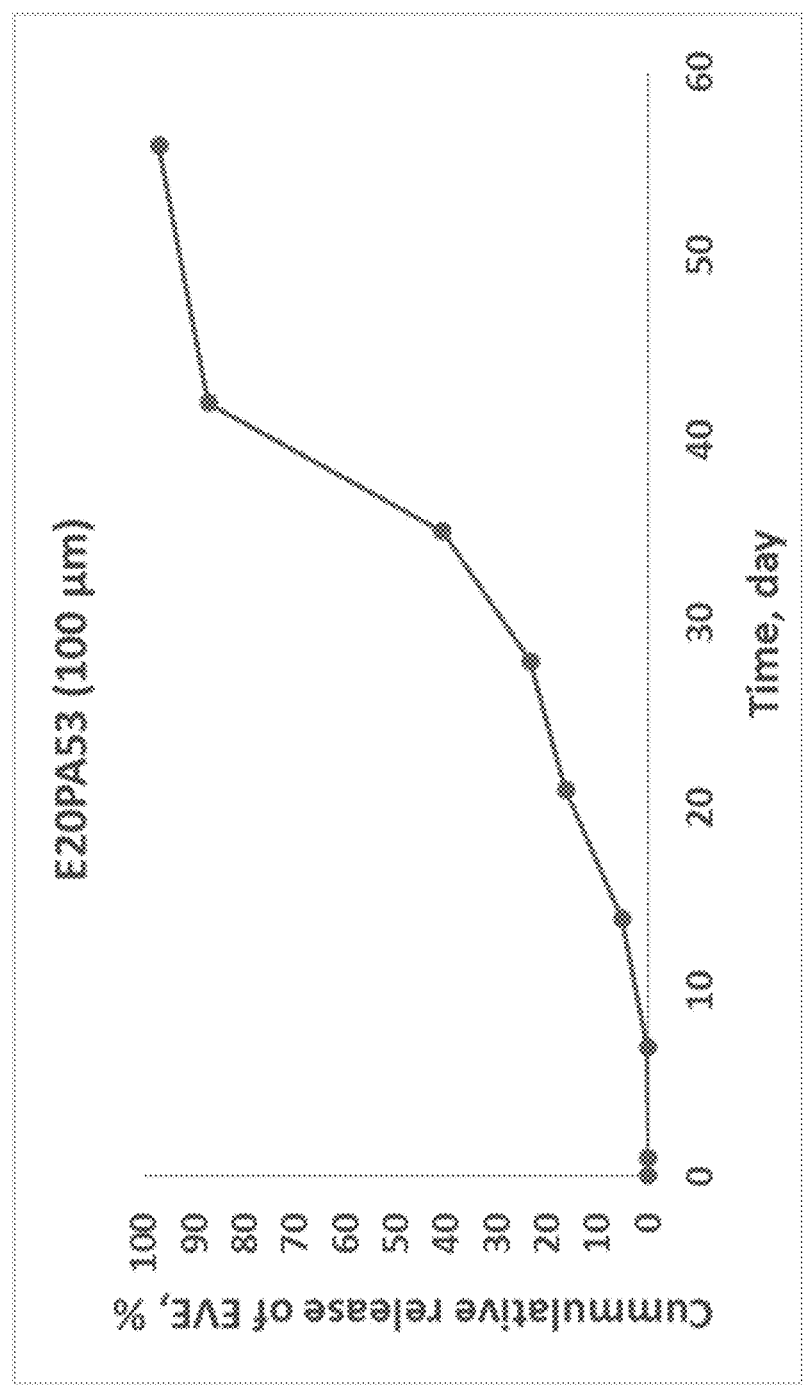
FIG. 6 is a line graph depicting the in vitro release profile of everolimus from EVE-loaded, 50 μm membrane PLGA microspheres.

FIG. 6 is a line graph depicting the in vitro release profile of everolimus from EVE-loaded PLGA microspheres.

E20PA53 microspheres containing everolimus (prepared with 50 μm membrane) were used for this release profile study, over a period of about 10-00 days. The microspheres had a diameter larger than 75 μm. The release profile depicted in FIG. 6 shows that this type of microsphere released less than 1% of everolimus from the microsphere during the first 7 days.

In case of PTX, the PTX-PLGA MS were prepared with a target drug loading of 15% (P15PA53 and P15PE77) and actual loading contents for the PTX-PLGA MS were found to be around 12-13%. PTX content was analyzed by HPLC method as described previously, and shown in FIG. 1B. The standard curve for PTX was prepared by HPLC method at 0.16-100 μg/mL concentration range (shown in FIG. 2B) and correlation coefficient (R) was 0.9998. Further, the microspheres prepared by using 30 μm pore size had 45 μm mean size and a spherical morphology shown by optical microscope (FIGS. 4A-4B). It was known that the actual size of microsphere was bigger than membrane size, but homogenous.

Figure 7:
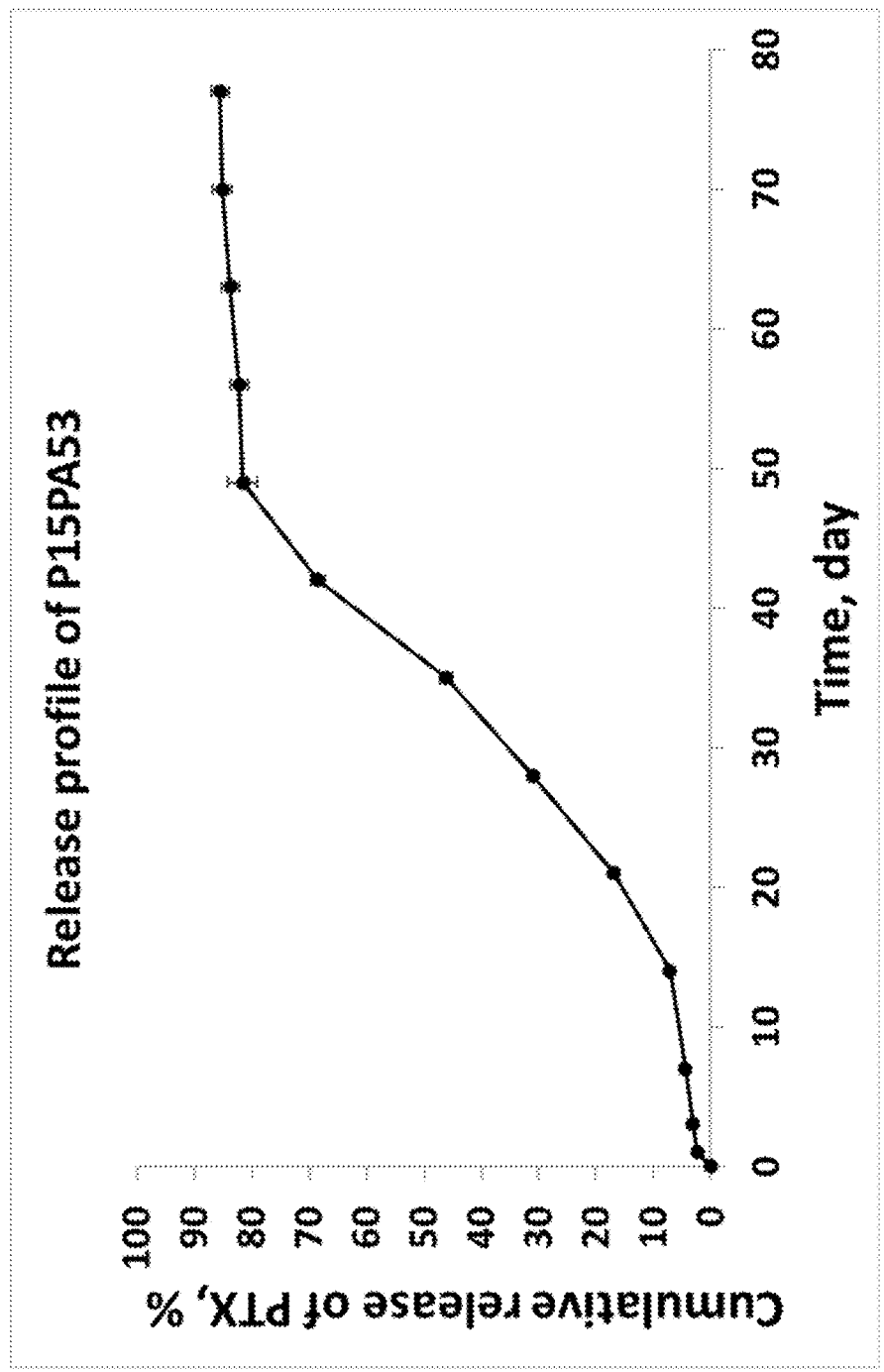
FIG. 7 is a line graph depicting the results of an in vitro release profile study of PTX-loaded PLGA microspheres, over the course of about 75-80 days.

FIG. 7 is a line graph depicting the results of an in vitro release profile study of PTX-loaded PLGA microspheres, over the course of about 75-80 days. P15PA53 type microspheres were used for this study. To analyze the release profile of PTX from the microspheres, an in vitro release study was performed by a sample-and-separate method at physiological conditions. As shown in FIG. 7, over 80% of the drug release from PTX-loaded PLGA microsphere (P15PA53) was observed by 49 days of incubation. On the other hand, ester-terminated PLGA-loading PTX (P15PE77) microsphere showed only around 15% drug release by 90 days (data not shown) and the remaining PTX was found still in the microspheres, which indicates a strong interaction between drug and polymer. As compared to EVE, the release rate of PTX from the microsphere was very slow even when the same polymer is used, which could be associated with PTX's strong hydrophobicity. The burst release of the drugs at 24 h is under 15%, which meets with the FDA's requirements (FIGS. 5, 6 and 7).

Example 3: In Vivo Mice Model Study of Tumor Recurrence after Treatment with Targeted or Chemotherapy Drugs Groups of seven 8-week-old female athymic NU/NU (immunodeficient) mice were inoculated subcutaneously with $2.5 \times 10^6$ MCF-7 cells for Groups 1-3, and groups of five 8-week-old female athymic NU/NU mice with $8 \times 10^6$ MCF-7 cells for Groups 4-6. After the tumor volume became about 200 mm$^3$, approximately 95% of the tumor was excised by a surgical knife. Next, EVE- or PTX-PLGA MS were suspended in diluent (0.5% carboxymethyl cellulose and 0.1% tween 20 in 10 mM PBS buffer). The resulting suspension was drawn into a syringe and painted into the excised surface. The treated site was sutured for closure after local treatment in accordance with the group assignment summarized in Table 1 below.

TABLE 1

Mice Groups and Treatment Protocols

| Group # | Estradiol Supplement | Local treatment | Oral hormone treatment |
|---|---|---|---|
| 1 | 40 μg daily | Diluent | Diluent |
| 2 | 40 μg daily | EVE-PLGA MS (30 mg/kg) | Tamoxifen (25 mg/kg daily) |
| 3 | 40 μg daily | PTX-PLGA MS (120 mg/kg) | Tamoxifen (25 mg/kg daily) |
| 4 | None | Diluent | Diluent |
| 5 | None | EVE-PLGA MS (30 mg/kg) | Exemestane (25 mg/kg daily) |
| 6 | None | PTX-PLGA MS (120 mg/kg) | Exemestane (25 mg/kg daily) |

After treatment, tumor growth of each mouse was measured with a caliper on Day 15 and expressed in mm$^3$ by the formula for the volume of a prolate ellipsoid (length×width×2π/6). There were 7 mice out of 7 mice showing recurring cancer for Group 1 (100%) while 2 mice out of 7 mice showing recurring cancer for Groups 2 and 3 (29%). There were 4 mice out of 5 mice (80%) showing recurring cancer for Group 4 while 2 mice out of 5 (40%) and 1 out of 5 (20%) mice showing recurring cancer for Groups 5 and 6, respectively. These results are summarized in Table 2 below.

TABLE 2

Recurring Cancer in Treated Mice

| Group # | Number of mice with recurring cancer/ Number of mice treated | % of recurring cancer |
|---|---|---|
| 1 | 7/7 | 100% |
| 2 | 2/7 | 29% |
| 3 | 2/7 | 29% |
| 4 | 4/5 | 80% |
| 5 | 2/5 | 40% |
| 6 | 1/5 | 20% |

This study clearly demonstrated that treatment with a sustained release of a targeted drug (everolimus) or a chemotherapy drug (paclitaxel) from PLGA microspheres along with a hormone modulator such as exemestane or tamoxifen after surgery reduced the rate of recurring cancer.

It may be advantageous to set forth definitions of certain words and phrases used in this patent document. The term "couple" and its derivatives refer to any direct or indirect communication between two or more elements, whether or not those elements are in physical contact with one another. The term "or" is inclusive, meaning and/or. As used in this application, "and/or" means that the listed items are alternatives, but the alternatives also include any combination of the listed items.

The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

Further, as used in this application, "plurality" means two or more. A "set" of items may include one or more of such items. The terms "comprising," "including," "carrying," "having," "containing," "involving," and the like are to be understood to be open-ended, i.e., to mean including but not limited to. Only the transitional phrases "consisting of" and "consisting essentially of," respectively, are closed or semi-closed transitional phrases.

Throughout this description, the aspects, embodiments or examples shown should be considered as exemplars, rather than limitations on the apparatus or procedures disclosed. Although some of the examples may involve specific combinations of method acts or system elements, it should be understood that those acts and those elements may be combined in other ways to accomplish the same objectives.

Acts, elements and features discussed only in connection with one aspect, embodiment or example are not intended to be excluded from a similar role(s) in other aspects, embodiments or examples.

Aspects, embodiments or examples of the invention may be described as processes, which are usually depicted using a flowchart, a flow diagram, a structure diagram, or a block diagram. Although a flowchart may depict the operations as a sequential process, many of the operations can be performed in parallel or concurrently. In addition, the order of the operations may be re-arranged. With regard to flowcharts, it should be understood that additional and fewer steps may be taken, and the steps as shown may be combined or further refined to achieve the described methods.

Although aspects, embodiments and/or examples have been illustrated and described herein, someone of ordinary skills in the art will easily detect alternate of the same and/or equivalent variations, which may be capable of achieving the same results, and which may be substituted for the aspects, embodiments and/or examples illustrated and described herein, without departing from the scope of the invention. Therefore, the scope of this application is intended to cover such alternate aspects, embodiments and/or or examples.

What is claimed is:

1. A method for treating a patient having a wound area resulting from surgical resection of a cancer mass, the method comprising:
   administering to the entirety of the wound area a composition before the wound area is closed, the composition comprising a first plurality of micro-particles comprising PLGA and one or more cancer treatment drugs, wherein the one or more cancer treatment drugs comprises everolimus, wherein the everolimus is 5-14%, and the first plurality of micro-particles comprising a molecular weight of 15 kDa-30 kDa, and a second plurality of micro-particles comprising PLGA and one or more wound healing drugs; and
   administering orally to the patient a hormone modulator selected from exemestane and tamoxifen;
   wherein the PLGA of the second plurality of micro-particles has a first ratio of PLA:PGA of 50:50, and is selectively adapted to release the one or more wound healing drugs for a first period of time;
   wherein the PLGA of the first plurality of micro-particles has a second ratio of PLA:PGA of 75:25, and is selectively adapted to release the one or more cancer treatment drugs for a second period of time, and wherein the first plurality of micro-particles comprises an increased physical size of a diameter of size of about 75 μm or larger to induce a reduced rate of release of the one or more cancer treatment drugs during the second period of time;
   wherein the first period of time is shorter than the second period of time due to the first ratio of PLA:PGA being smaller than the second ratio of PLA to PGA, and begins about 7 days after the administering step, and wherein the first plurality of micro-particles releases about 1% or less of the one or more cancer treatment drugs before the second period of time begins;
   wherein the first period of time partially overlaps with a beginning of the second period of time;
   and wherein the first plurality of micro-particles is coated with a biodegradable polymer, such that to reduce an initial burst release of the cancer treatment drug by the first plurality of micro-particles.

2. The method of claim 1, wherein the first plurality of micro-particles and the second plurality of micro-particles are mixed at a ratio of less than 0.5 by weight.

3. The method of claim 1, wherein the first plurality of micro-particles has an increased physical size to induce a reduced rate of release of the one or more cancer drugs during the second period of time.

4. The method of claim 3, wherein the first plurality of micro-particles has a diameter size of about 75 μm or larger.

5. The method of claim 1, wherein the second plurality of micro-particles has a decreased physical size to induce an increased rate of release of the one or more wound drugs during the first period of time.

6. The method of claim 1, wherein the PLGA of the second plurality of micro-particles has a decreased molecular weight to induce an increased rate of release of the one or more wound drugs during the first period of time.

* * * * *